(12) United States Patent
Jordine et al.

(10) Patent No.: US 7,683,048 B2
(45) Date of Patent: Mar. 23, 2010

(54) POLYMORPHIS OF A KNOWN THIOPHENECARBOXYLIC ACID DODECAHYDROCYCLOPENTA (A) PHENANTHRENYL ESTER

(75) Inventors: Guido Jordine, Freiburg (DE); Michael Mutz, Freiburg i. Br. (DE)

(73) Assignee: Novartis AG, Basel (CH)

( * ) Notice: Subject to any disclaimer, the term of this patent is extended or adjusted under 35 U.S.C. 154(b) by 1275 days.

(21) Appl. No.: 10/522,358

(22) PCT Filed: Jul. 28, 2003

(86) PCT No.: PCT/EP03/08314
§ 371 (c)(1),
(2), (4) Date: Jun. 27, 2005

(87) PCT Pub. No.: WO2004/013156
PCT Pub. Date: Feb. 12, 2004

(65) Prior Publication Data
US 2006/0166954 A1 Jul. 27, 2006

(30) Foreign Application Priority Data
Jul. 29, 2002 (GB) .............................. 0217504.0

(51) Int. Cl.
*A61K 31/58* (2006.01)
*C07D 215/04* (2006.01)

(52) U.S. Cl. ........................................ 514/172; 540/2

(58) Field of Classification Search .................. 514/172; 540/2
See application file for complete search history.

(56) References Cited

FOREIGN PATENT DOCUMENTS

| WO | 02/00679 | | 1/2002 |
|---|---|---|---|
| WO | WO 02/00679 | * | 1/2002 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26) state "Predicting the formation of solvates or hydrates of a compound and the number of molecules of water or solvent incorporated in to the crystal lattice of a compound is complex and difficult."*
Caira, "Crystalline Polymorphism of Organic Compounds", Current Chemistry, vol. 198, pp. 163-208 (1998).
Haleblian et al., "Pharmaceutical Applications of Polymorphism", Journal of Pharmaceutical Sciences, vol. 58, No. 8, pp. 911-929 (1969).

* cited by examiner

*Primary Examiner*—Barbara P Badio
(74) *Attorney, Agent, or Firm*—Cozette M McAvoy

(57) ABSTRACT

Polymorphic crystal forms of 3-methylthiophene-2-carboxylic acid (6S,9R,10S,11S,13S,16R, 17R)-9-chloro-6-fluoro-11-hydroxy-17-methoxycarbonyl-10,13,16-trimethyl-3-oxo-6,7,8,9,10, 11,12,13,14,15,16,17-dodecahydro-3H-cyclopenta[a]phenanthren-17-yl ester. The crystal forms possess anti-inflammatory activity and have very good stability. Methods for preparing the crystal forms are also described.

10 Claims, 1 Drawing Sheet

POLYMORPHIS OF A KNOWN THIOPHENECARBOXYLIC ACID DODECAHYDROCYCLOPENTA (A) PHENANTHRENYL ESTER

This invention relates to new polymorphic crystal forms of a compound of formula I and methods for preparing them.

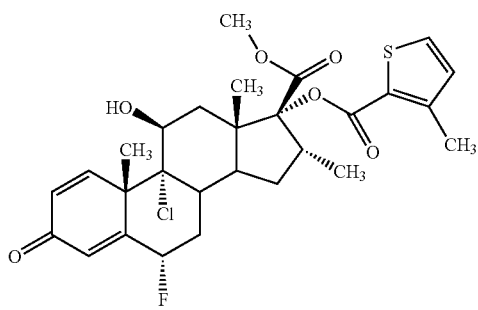

The compound of formula I, namely 3-methylthiophene-2-carboxylic acid (6S,9R,10S,11S, 13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl ester, possesses a high anti-inflammatory activity. This activity can be demonstrated by its inhibition of TNF-alpha synthesis and release in a human macrophage cell line and by its inhibition of inflammatory conditions, particularly in the airways, e.g. inhibition of eosinophil activation, in animal models, e.g. mouse or rat models of airways inflammation, for example as described by Szarka et al, J. Immunol. Methods (1997) 202:49-57; Renzi et al, Am. Rev. Respir. Dis. (1993) 148:932-939; Tsuyuki et al., J. Clin. Invest. (1995) 96:2924-2931; and Cernadas et al (1999) Am. J. Respir. Cell Mol. Biol. 20:1-8.

This compound has been investigated for use as a pharmaceutical. The existence of various crystallisation polymorphic forms of the compound has been explored in order to determine the most appropriate form of the compound for the proposed use.

Novel crystal forms of the compound of formula I have now been isolated. Some of these novel crystal forms have very good stability, facilitating their use in the preparation of pharmaceutical dosage forms.

Figure 1:
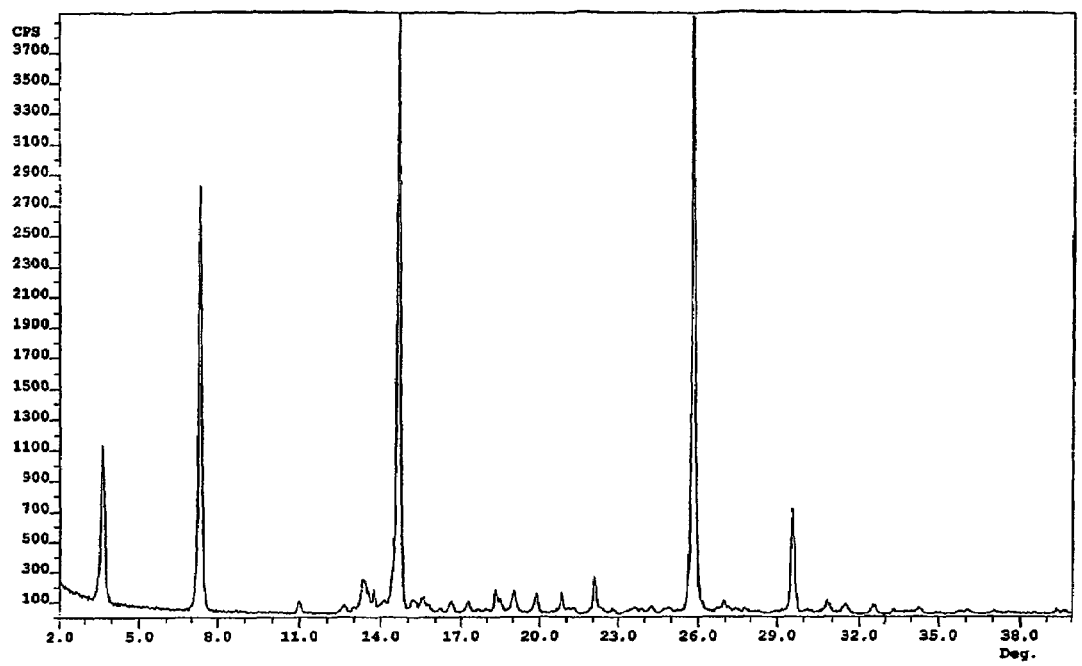
FIG. 1 is an X-ray powder diffraction pattern of Crystal form A of the compound of formula I.

Accordingly, the present invention provides in one aspect a compound of formula I

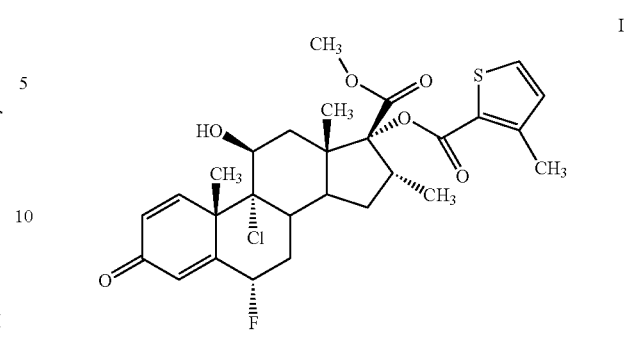

in a crystal form A that has a melting point, by Differential Scanning Calorimetry, of about 264° C. with simultaneous decomposition, at a heating rate of 20° C./min and the following characteristic diffraction lines (2θ in angular degrees±0.2°) in the X-ray diffraction pattern thereof: 3.6°, 7.3°, 13.4°, 14.6°, 18.3°, 22.0°, 25.8°, 25.9°, 29.5°; or in a crystal form B that has a melting point, by Differential Scanning Calorimetry, of about 270° C. with simultaneous decomposition, at a heating rate of 20° C./min and the following characteristic diffraction lines (2θ in angular degrees±0.2°) in the X-ray diffraction pattern thereof: 7.2°, 9.3°, 12.0°, 12.8°, 13.1°, 14.5°, 17.4°, 20.4°, 23.2° and 25.8°.

Crystal form A may be prepared by crystallising the compound of formula I from a solution thereof in an organic solvent such as isopropanol, ethyl acetate, n-butanol, hexane, heptane, tert-butylmethylether, toluene or tetrahydrofuran, for example by equilibrating the compound in that solvent over 24 hours at 25° C., or analogously such as hereinafter described in Example 1. The crystallisation may be induced by, for example, cooling a supersaturated solution of the compound of formula I in the solvent, or by adding to the solution of the compound of formula I a solvent in which the compound of formula I is less soluble. The starting solution of the compound of formula I may be at ambient or elevated (up to reflux) temperature.

Crystal form B may be prepared by crystallising the compound of formula I from a solution thereof in a polar organic solvent such as ethanol, methanol or methylene chloride, for example by equilibrating the compound in that solvent over 24 hours at 25° C., or analogously such as hereinafter described in Example 2. The crystallisation may be induced by, for example, cooling a supersaturated solution of the compound of formula I in the polar solvent, or by adding to the solution of the compound of formula I a polar solvent in which the compound of formula I is less soluble. The starting solution of the compound of formula I may be at ambient or elevated (up to reflux) temperature.

For the preparation of each of the crystal forms, working up may be carried out generally using known procedures for the separation of the crystallisate from the mother liquor, for example by filtration, with or without the assistance of pressure and/or vacuum, or by centrifugation, and subsequent drying of the crystallisate.

In the presence of ethanol crystal form A converts to crystal form B. In the presence of isopropanol crystal form B converts to crystal form A.

The crystal forms can be distinguished in particular by their X-ray powder diagrams. X-ray diagrams taken with a diffractometer and using Cu-Kα$_1$-radiation are preferably used to characterise solids of organic compounds. X-ray powder diffraction diagrams are particularly useful to determine the crystal form or modification of the compound of formula I. The use of such diagrams is described in the accompanying Examples.

Crystal form A appears to be more thermodynamically stable than crystal form B in the solid state. However, in suspension with solvents the stability is solvent dependent.

The compound of formula I may be prepared in accordance with the method given in Example 26 of international patent application WO 02/00679.

Given its anti-inflammatory activity, the compound of formula I in crystal form A or B is useful in the treatment of inflammatory conditions, particularly inflammatory or obstructive airways diseases. Treatment in accordance with the invention may be symptomatic or prophylactic.

Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".) Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to its anti-inflammatory activity, in particular in relation to inhibition of eosinophil activation, the compound of formula I in crystal form A or B is also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

The compound of formula I in crystal form A or B is also useful in the treatment of inflammatory conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory conditions of the skin.

The compound of formula I in crystal form A or B may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, diseases of the joints such as rheumatoid arthritis and inflammatory bowel disease such as ulcerative colitis and Crohn's disease.

The compound of formula I in crystal form A or B is also useful as a co-therapeutic agent for use in conjunction with other drug substances for treatment of airways diseases, particularly bronchodilatory or anti-inflammatory drug substances, particularly in the treatment of obstructive or inflammatory airways diseases such as those mentioned hereinbefore, for example as potentiators of therapeutic activity of such drugs or as a means of reducing required dosaging or potential side effects of such drugs. The compound of formula I in crystal form A or B may be mixed with the other drug in a fixed pharmaceutical composition or it may be administered separately, before, simultaneously with or after the other drug.

Such anti-inflammatory drugs include steroids, in particular glucocorticosteroids such as budesonide, beclamethasone dipropionate, fluticasone propionate, ciclesonide or mometasone furoate and compounds described in WO 0200679, WO 0288167, WO 0212266 and WO 02100879; LTB4 antagonists such as those described in U.S. Pat. No. 5,451,700; LTB4 antagonists such as those described in U.S. Pat. No. 5,451,700; LTD4 antagonists such as montelukast and zafirlukast; dopamine receptor agonists such as cabergoline, bromocriptine, ropinirole and 4-hydroxy-7-[2-[[2-[[3-(2-phenylethoxy)-propyl]sulfonyl]ethyl]amino]ethyl]-2(3H)-benzothiazolone and pharmaceutically acceptable salts thereof (the hydrochloride being VIOZAN® (sibenadet HCl)—AstraZeneca); PDE4 inhibitors such as ARIFLO® (cilomilast) (GlaxoSmith Kline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene) and KW-4490 (Kyowa Hakko Kogyo); A2a agonists such as those described in EP 1052264, EP 1241176, WO 0023457, WO 0077018, WO 0123399, WO 0160835, WO 0194368, WO 0200676, WO 0222630, WO 0296462, WO 0127130, WO 0127131, WO 9602543, WO 9602553, WO 9828319, WO 9924449, WO 9924450, WO 9924451, WO 9938877, WO 9941267, WO 9967263, WO 9967264, WO 9967265, WO 9967266, WO 9417090, EP 409595A2 and WO 0078774; and A2b antagonists such as those described in WO 02/42298.

Such bronchodilatory drugs include anticholinergic or antimuscarinic agents, such as those described in EP 424021, U.S. Pat. No. 5,171,744 (Pfizer) and WO 01/04118 (Almirall Prodesfarma) and but in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International Publication No. WO 00/75114, which document is incorporated herein by reference, preferably compounds of the Examples thereof, especially a compound of formula

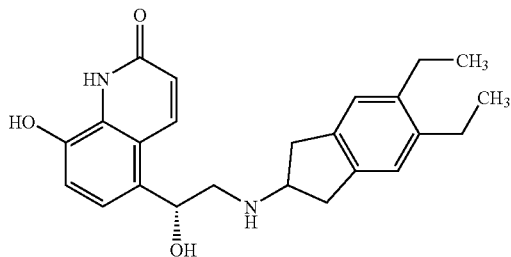

in free or pharmaceutically acceptable salt or solvate form.

Combinations of the compound of formula I in crystal form A or B and beta-2 agonists, PDE4 inhibitors or LTD4 antagonists may be used, for example, in the treatment of COPD or, particularly, asthma.

Combinations of the compound of formula I in crystal form A or B and anticholinergic or antimuscarinic agents, PDE4 inhibitors, LTB4 antagonists may be used, for example, in the treatment of asthma or, particularly, COPD.

In accordance with the foregoing, the invention also provides a method for the treatment of an inflammatory condition, particularly an inflammatory or obstructive airways disease, which comprises administering to a subject, particularly a human subject, in need thereof an effective amount of the compound of formula I in crystal form A or B as hereinbefore described. In another aspect the invention provides the use of the compound of formula I in crystal form A or B for the manufacture of a medicament for the treatment of an inflammatory condition, particularly an inflammatory or obstructive airways disease.

The compound of formula I in crystal form A or B may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient the compound of formula I in crystal form A or B optionally together with a pharmaceutically acceptable diluent or carrier therefor. The composition may contain a co-therapeutic agent such as a bronchodilatory or anti-inflammatory drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I in crystal form A or B having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I in crystal form A or B either dissolved, or suspended, in a vehicle containing water, a co-solvent such as ethanol or propylene glycol and a stabiliser, which may be a surfactant.

The invention includes (A) the compound of formula I in crystal form A or B in inhalable form, e.g. in an aerosol or other atomisable composition or in inhalable particulate, e.g. micronised, form, (B) an inhalable medicament comprising the compound of formula I in crystal form A or B in inhalable form; (C) a pharmaceutical product comprising the compound of formula I in crystal form A or B in inhalable form in association with an inhalation device; and (D) an inhalation device containing the compound of formula I in crystal form A or B in inhalable form.

Dosages of the compound of formula I in crystal form A or B employed in practising the present invention will of course vary depending, for example, on the particular condition to be treated, the effect desired and the mode of administration. In general, suitable daily dosages for administration by inhalation are of the order of 0.005 to 10 mg, while for oral administration suitable daily doses are of the order of 0.05 to 100 mg.

The invention is illustrated by the following Examples.

EXAMPLE 1

Preparation and Characterisation of Crystal Form A 50 mg of the compound of formula I is equilibrated in 1 ml isopropanol over 24 hours at 25° C. The product is filtered and dried. After drying the compound of formula I is obtained in the form of white crystals.

Measurements are made by X-ray powder diffraction and using Cu—K$\alpha_1$. The X-ray diffraction pattern thus determined, as represented by the reflection lines and intensities of the most important lines, is shown in FIG. 1 and characterised in Table 1 below.

TABLE 1

X-ray diffraction lines and intensities for crystal form A

| 2θ | Intensity |
|---|---|
| 3.6 | medium |
| 7.3 | strong |
| 13.4 | medium |
| 14.6 | strong |
| 18.3 | medium |

TABLE 1-continued

X-ray diffraction lines and intensities for crystal form A

| 2θ | Intensity |
|---|---|
| 22.0 | medium |
| 25.8 | strong |
| 25.9 | medium |
| 29.5 | medium |

EXAMPLE 2

Preparation and Characterisation of Crystal Form B 87 mg of the compound of formula I are equilibrated in 2 ml ethanol over 24 hours at 25° C. The product is filtered and dried. After drying the compound of formula I is obtained in the form of white crystals.

Figure 2:
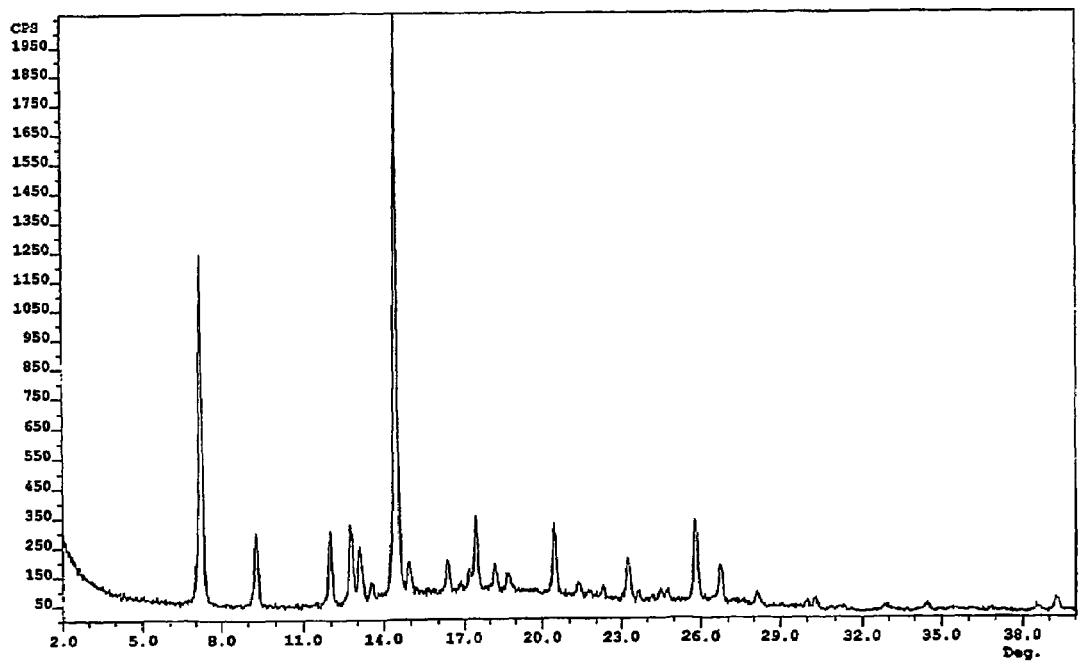
FIG. 2 is an X-ray powder diffraction pattern of Crystal from B of the compound of formula I.

Measurements are made by X-ray powder diffraction and using Cu-K$\alpha_1$. The X-ray diffraction pattern thus determined, as represented by the reflection lines and intensities of the most important lines, is shown in FIG. 2 and characterised in Table 2 below.

TABLE 2

X-ray diffraction lines and intensities for crystal form B

| 2θ | Intensity |
|---|---|
| 7.2 | strong |
| 9.3 | Medium |
| 12.0 | Medium |
| 12.8 | Medium |
| 13.1 | Medium |
| 14.5 | Strong |
| 17.4 | Medium |
| 20.4 | Medium |
| 23.2 | Medium |
| 25.8 | Medium |

EXAMPLE 3

Preparation of Crystal Forms A and B in Various Solvents 8 mg of the compound of formula I are equilibrated with 1.5 ml of a variety of solvents for at least 24 hours in a water bath at 25° C.±0.1. The solutions are filtered and dried for 10 minutes in the air. The solid part is investigated by X-ray powder diffraction (XRPD) to identify the crystal form produced. The results are shown in Table 3 below.

The procedure is repeated at 50° C.±0.1 and 70° C.±0.1 and the results are shown in Tables 4 and 5 respectively.

TABLE 3

Equilibration with solvent at 25° C.

| Solvent | XRPD |
|---|---|
| n-Butanol | Crystal form A |
| Ethanol | Crystal form B |
| Ethyl acetate | Crystal form A |
| Isopropanol | Crystal form A |
| Hexane | Crystal form A |
| Heptane | Crystal form A |
| Methanol | Crystal form B |
| Methylene chloride | Crystal form B |
| Tert-butylmethylether | Crystal form A |
| Toluene | Crystal form A |

TABLE 3-continued

Equilibration with solvent at 25° C.

| Solvent | XRPD |
|---|---|
| Tetrahydrofuran | Crystal form A |
| Water | Crystal forms A + B |

TABLE 4

Equilibration with solvent at 50° C.

| Solvent | XRPD |
|---|---|
| n-Butanol | Crystal form A |
| Ethanol | Crystal form B |
| Ethyl acetate | Crystal form A |
| Isopropanol | Crystal form A |
| Hexane | Crystal form A |
| Heptane | Crystal form A |
| Methanol | Crystal form B |
| Methylene chloride | Crystal form B |
| Tert-butylmethylether | Crystal form A |
| Tetrahydrofuran | Crystal form A |
| Toluene | Crystal form A |
| Water | Crystal forms A + B |

TABLE 5

Equilibration with solvent at 70° C.

| Solvent | XRPD |
|---|---|
| n-Butanol | Crystal form A |
| Ethanol | Crystal form B |
| Isopropanol | Crystal form A |

These results show that the choice of solvent dictates which crystal form of the compound of formula I is formed.

EXAMPLE 4

Stability of Crystal Forms A and B

Samples of the compound of formula I in crystal form A, the compound of formula I in crystal form B, a mixture of both crystal forms and an amorphous form of the compound of formula I (obtained by spray drying) are stored for 4 weeks at 80° C. under different conditions and analyzed by X-ray powder diffraction (XRPD). The results are shown in Table 6 below.

TABLE 6

Stability after 4 weeks at 80° C.

| Conditions | Sealed | 75% r.h.* open | N$_2$ | N$_2$ + 2% water | O$_2$ |
|---|---|---|---|---|---|
| Crystal form A | A | A | A | A | A |
| Crystal form B | B | A + B | B | A + B | A + B |
| Crystal forms A + B | A + B | A + B | A + B | A + B | A + B |
| Amorphous form | A | A | A | A | A |

*relative humidity

These results show that crystal form B can convert at least partially in the solid state into crystal form A when stored for 4 weeks at 80° C. The amorphous form can also convert into crystal form A. This suggests crystal form A is more thermodynamically stable than crystal form B.

EXAMPLE 5

Heat of Solution Experiments

The heat of solution of samples of crystal forms A and B of the compound of formula I are measured at 25° C. in acetone. The results are shown in Table 7 below.

TABLE 7

| Heat of solution at 25° C. in acetone | |
|---|---|
| Crystal form | Heat of solution (J/g) |
| A | 29.3 |
| B | 17.9 |

These results show crystal form A has a higher endothermic heat of solution compared with crystal form B. This indicates crystal form A is more thermodynamically stable than crystal form B.

The invention claimed is:

1. A compound of formula I

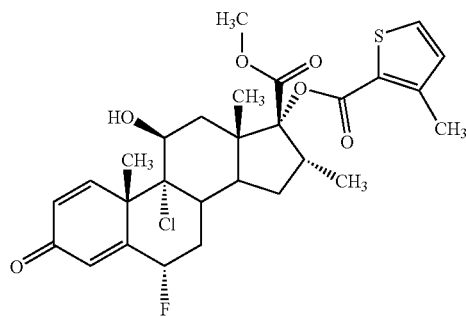

in a crystal form B that has a melting point, by Differential Scanning Calorimetry, of about 270° C. with simultaneous decomposition, at a heating rate of 20° C./min and the following characteristic diffraction lines (2θ in angular degrees±0.2°) in the X-ray diffraction pattern thereof: 7.2°, 9.3°, 12.0°, 12.8°, 13.1°, 14.5°, 17.4°, 20.4°, 23.2° and 25.8°.

2. A pharmaceutical composition comprising, as active ingredient, an effective amount of the compound of formula I in crystal form B as defined in claim 1, optionally together with a pharmaceutically acceptable carrier.

3. A composition according to claim 2, which is in inhalable form.

4. A pharmaceutical composition comprising a compound of formula I as defined in claim 1 in combination with another drug substance which is an anti-inflammatory or a bronchodilator.

5. A composition according to claim 4 wherein the another drug substance is a beta-2 adrenoceptor agonist.

6. A composition according to claim 5 wherein the beta-2 adrenoceptor agonist is selected from the group consisting of salbutamol, terbutaline, salmeterol, formoterol and the compound of formula

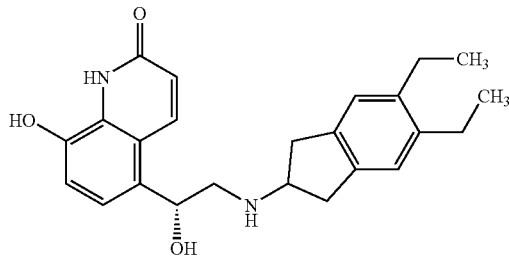

in free or pharmaceutically acceptable salt form.

7. A method of treating an inflammatory or obstructive airways disease in a subject in need of such treatment, which comprises administering to said subject an effective amount of a compound according to claim 1 in crystal form B as defined in claim 1.

8. A method of treating asthma or chronic obstructive pulmonary disease in a subject in need of such treatment, which comprises administering to said subject an effective amount of a compound according to claim 1 in crystal form B as defined in claim 1.

9. A method of treating atopic dermatitis in a subject in need of such treatment, which comprises administering to said subject an effective amount of a compound according to claim 1 in crystal form B as defined in claim 1.

10. A method of preparing a compound of formula I in crystal form B as defined in claim 1 which comprises crystallising the compound of formula I as defined in claim 1 from a solution thereof in ethanol, methanol or methylene chloride.

* * * * *